(12) United States Patent
Shi et al.

(10) Patent No.: US 11,259,937 B2
(45) Date of Patent: Mar. 1, 2022

(54) CERVICAL VERTEBRA FIXING PLATE MAINTAINING NATURAL HEIGHT, CERVICAL VERTEBRA ANTERIOR FIXATION AND FUSION SYSTEM MAINTAINING NATURAL HEIGHT AND METHOD THEREOF

(71) Applicant: Shanghai Changzheng Hospital, Shanghai (CN)

(72) Inventors: Jiangang Shi, Shanghai (CN); Jingchuan Sun, Shanghai (CN); Dan Han, Shanghai (CN); Kai Chen, Shanghai (CN); Shunmin Wang, Shanghai (CN)

(73) Assignee: SHANGHAI CHANCZHENG HOSPITAL, Shanghai (CN)

( * ) Notice: Subject to any disclaimer, the term of this patent is extended or adjusted under 35 U.S.C. 154(b) by 40 days.

(21) Appl. No.: 16/677,845

(22) Filed: Nov. 8, 2019

(65) Prior Publication Data

US 2020/0146839 A1 May 14, 2020

(30) Foreign Application Priority Data

Nov. 9, 2018 (CN) .......................... 201811329220.3
Nov. 9, 2018 (CN) .......................... 201811329248.7

(51) Int. Cl.
*A61F 2/44* (2006.01)
*A61B 17/70* (2006.01)

(52) U.S. Cl.
CPC ........ *A61F 2/4455* (2013.01); *A61B 17/7001* (2013.01); *A61B 17/7059* (2013.01)

(58) Field of Classification Search
CPC ............ A61F 2/4455; A61F 2/44–447; A61B 17/7001; A61B 17/7059; A61B 17/80–8095
See application file for complete search history.

(56) References Cited

U.S. PATENT DOCUMENTS 5,951,558 A * 9/1999 Fiz ..................... A61B 17/8042
606/291
6,152,927 A * 11/2000 Farris ................. A61B 17/7059
606/287

(Continued)

FOREIGN PATENT DOCUMENTS

CN          103099662 A     5/2013
CN          205286618 U     6/2016

(Continued)

*Primary Examiner* — Nicholas J Plionis
(74) *Attorney, Agent, or Firm* — Frost Brown Todd LLC (57) ABSTRACT

The present disclosure relates to a cervical vertebra anterior fixation and fusion system maintaining natural height and the fixing plate. The fixing plate is provided with a plate body, wherein the plate body is provided with windows, locking members and screw fixing holes to be matched with screws. A minimum distance between an upper side wall and a lower side wall of the window in a vertical axis direction is 3-8 mm; and a minimum distance between a left side wall and a right side wall of the window in a transverse axis direction is 12.1-18 mm. The present disclosure further relates to a method for performing anterior cervical intervertebral disc resection and fusion by applying the fixation and fusion system.

11 Claims, 9 Drawing Sheets

(56) References Cited

U.S. PATENT DOCUMENTS

| | | | | |
|---|---|---|---|---|
| 7,309,340 | B2* | 12/2007 | Fallin | A61B 17/7059 606/104 |
| 7,625,375 | B2* | 12/2009 | Garden | A61B 17/7059 606/86 B |
| 7,740,649 | B2* | 6/2010 | Mosca | A61B 17/8863 606/289 |
| 7,815,681 | B2* | 10/2010 | Ferguson | A61F 2/4455 623/17.16 |
| 8,454,667 | B2* | 6/2013 | Humphreys | A61B 17/8042 606/289 |
| 8,906,077 | B2* | 12/2014 | Bush, Jr. | A61B 17/8042 606/296 |
| 10,016,224 | B2* | 7/2018 | Altarac | A61B 17/7059 |
| 10,064,666 | B2* | 9/2018 | Dunaway | A61B 17/80 |
| 10,405,900 | B2* | 9/2019 | Ha | A61B 17/7059 |
| 2002/0183755 | A1* | 12/2002 | Michelson | A61B 17/7059 606/71 |
| 2003/0187509 | A1* | 10/2003 | Lemole, Jr. | A61B 17/7059 623/17.16 |
| 2004/0039387 | A1* | 2/2004 | Gause | A61B 17/1735 606/86 B |
| 2004/0260306 | A1* | 12/2004 | Fallin | A61B 17/866 606/104 |
| 2005/0033294 | A1* | 2/2005 | Garden | A61B 17/7059 623/17.11 |
| 2005/0101960 | A1* | 5/2005 | Fiere | A61F 2/4611 623/17.11 |
| 2005/0137597 | A1* | 6/2005 | Butler | A61B 17/7059 606/71 |
| 2006/0276897 | A1* | 12/2006 | Winslow | A61B 17/7059 623/17.11 |
| 2007/0270965 | A1* | 11/2007 | Ferguson | A61B 17/7059 623/17.11 |
| 2008/0215097 | A1* | 9/2008 | Ensign | A61B 17/7059 606/282 |
| 2012/0277803 | A1* | 11/2012 | Remesh | A61B 17/8042 606/289 |
| 2015/0112393 | A1* | 4/2015 | Garber | A61B 17/7058 606/279 |
| 2016/0128746 | A1* | 5/2016 | Dunaway | A61B 17/8042 606/246 |
| 2016/0262905 | A1* | 9/2016 | Prado | A61F 2/4637 |
| 2017/0065311 | A1* | 3/2017 | George | A61B 17/8033 |
| 2018/0103989 | A1* | 4/2018 | Altarac | A61B 17/80 |
| 2018/0271571 | A1* | 9/2018 | Johnson | A61B 17/8042 |
| 2019/0046245 | A1* | 2/2019 | Ha | A61B 17/7059 |

FOREIGN PATENT DOCUMENTS

| | | | |
|---|---|---|---|
| CN | 207400791 U | 5/2018 | |
| WO | WO-2017197317 A1 * | 11/2017 | A61B 17/70 |

* cited by examiner

CERVICAL VERTEBRA FIXING PLATE MAINTAINING NATURAL HEIGHT, CERVICAL VERTEBRA ANTERIOR FIXATION AND FUSION SYSTEM MAINTAINING NATURAL HEIGHT AND METHOD THEREOF

CROSS-REFERENCE TO RELATED APPLICATIONS

The present application claims the benefit of priority to the Chinese Patent Application No. 201811329248.7, filed on Nov. 9, 2018 and the Chinese Patent Application No. 201811329220.3, filed on Nov. 9, 2018, the entire contents thereof are incorporated herein by reference.

TECHNICAL FIELD

The present disclosure relates to the technical field of medical instruments, in particular to a cervical vertebra fixing plate maintaining natural height, and a cervical vertebra anterior fixation and fusion system maintaining natural height and a method thereof.

BACKGROUND

The treatment of the cervical intervertebral disc resection relates to: 1. patients having obvious damage to spinal cord, nerve root and vertebral artery due to cervical spondylitis and being in a situation that conservative treatment of the cervical spondylitis is ineffective; 2. patients with cervical spondylitis whose symptoms have suddenly aggravated due to trauma or other reasons; 3. patients with acute cervical disc herniation in a situation that there is no effect in non-surgical treatment; 4. patients with cervical spondylitis having obvious instability of a certain section of the cervical vertebra and obvious neck pain and being in a situation that it is ineffective through a normal non-surgical treatment, and even if the patients have no feeling of limbs and dyskinesia, they need to consider a surgical treatment to stop the predictable disease development.

A micro-resection of cervical intervertebral disc has two approaches, i.e., a posterior approach and an anterior approach. Taking an anterior cervical intervertebral disc resection and fusion as an example, the surgery includes the following steps: cutting to form an incision; exposing front of a vertebral body and an intervertebral disc; positioning; opening the vertebral body and resetting; removing the intervertebral disc; taking and implanting bones; fixing with a steel plate; and suturing the incision. However, in long-term clinical work, the inventor of the present application summarizes that the bone implanting fusion cage has a height larger than the height of the intervertebral disc to ensure the bone implanting fusion cage is extruded with adjacent vertebral bodies to facilitate osteogenesis, but at the same time, the space between the upper vertebral body and the lower vertebral body is distracted, so that the space between a plurality of intervertebral discs will be distracted too much if a plurality of intervertebral discs are resected, thereby causing the cervical vertebra to lose its natural height, and having surgical complications to cause a pain in the postoperative neck. At present, there is no report or solution to the above-mentioned technical problem.

After searching, Patent document CN205286618U (published on Jun. 8, 2016) discloses a cervical vertebra intervertebral fusion cage including a fusion cage body and a fixing device; the fusion cage body is provided with a cavity for filing bone which penetrates through upper and lower surfaces of the fusion cage body, and an outline of a vertical projection of the fusion cage body is arched. The fixing device includes an anterior fixing plate and locking screws, and the anterior fixing plate is detachably connected to the fusion cage body; the left end of the anterior fixing plate is provided with a first through hole, and the second through holes are located at the two sides of the first through hole and a diameter of the second through hole is equal to a diameter of the first through hole. An angle of the first through hole with respect to the horizontal direction and an angle of the second through hole with respect to the horizontal direction are complementary; and the locking screws are not closely matched with the first through hole and the second through hole. There are some advantages of obtaining stronger local biomechanical stability, effectively recovering and maintaining the physiological curvature of the cervical vertebra, and obviously improving the fusion rate. Patent document CN103099662A (published on May 15, 2013) discloses an anterior cervical unilateral fixing system for fixing an intervertebral fusion cage containing autologous bone or artificial bone and implanted into an intervertebral space on the adjacent lower vertebral body to treat interlocking of cervical facet joints; the anterior cervical unilateral fixing system includes: an anterior fixing plate, a bone screw and an intervertebral fusion cage screw; wherein the intervertebral fusion cage screw is used for fixedly connecting the intervertebral fusion cage containing autologous bone or artificial bone which is implanted into the intervertebral space and the anterior fixing plate together; the bone screw is arranged between the anterior fixing plate and the vertebral body and connects the anterior fixing plate and the vertebral body as a whole; the number of bone screws is two. There are advantages of better treating the interlocking of cervical facet joints, recovering the normal physiological curvature of the cervical vertebra and reducing the occurrence of complications. Patent document CN207400791U (published on May 25, 2018) discloses an anterior cervical steel plate including: a steel plate provided with fusion windows and a plurality of fixing holes, wherein the fixing holes are uniformly and symmetrically distributed on the steel plate body. There are advantages of the anterior cervical steel plate, and fixing the anterior cervical steel plate on the cervical vertebra by screws passing through the fixing holes; and providing fusion windows on the steel plate body. The surgery operator can clearly and directly observe vertebral body through the fusion window, which is convenient for confirming the position of bone implanting piece and steel plate.

However, no device capable of preventing the cervical vertebra from losing the natural height caused by the cervical intervertebral disc resection is available at present.

SUMMARY

The object of the present disclosure is to provide a cervical vertebra fixing plate maintaining natural height for the deficiencies in the prior art.

Another object of the present disclosure is to provide an anterior cervical fixation and fusion system maintaining natural height.

A further object of the present disclosure is to provide a method for anterior cervical discectomy and fusion (ACDF).

To achieve the first object, a technical solution applied by the present disclosure is as follows.

A cervical vertebra fixing plate maintaining natural height is provided. The cervical vertebra fixing plate includes a plate body provided with windows, locking members and screw fixing holes matched with screws; a size of the window allows the cervical implants to pass through.

Preferably, the minimum distance between an upper side wall and a lower side wall of the window in a vertical axis direction is 3-8 mm; and a minimum distance between a left side wall and a right side wall of the window in a transverse axis direction is 12.1-18 mm.

Preferably, the minimum distance between the upper side wall and the lower side wall of the window in the vertical axis direction is 4-8 mm, and the minimum distance between the left side wall and the right side wall of the window in the transverse axis direction is 14-18 mm.

More preferably, the minimum distance between the upper side wall and the lower side wall of the window in the vertical axis direction is 6-8 mm, and the minimum distance between the left side wall and the right side wall of the window in the transverse axis direction is 16-18 mm.

Preferably, the cervical implant is a fusion cage.

Preferably, the locking member includes a front rotating plate, a rear rotating plate and a rotating shaft, the front rotating plate for locking the screw is located at a front side of the plate body, and the rear rotating plate for locking the fusion cage is located at a rear side of the plate body.

More preferably, the rear rotating plate is a chamfered rectangular sheet, and is placed along the vertical axis when the cage is locked.

More preferably, the rear rotating plate is composed of two fan-shaped sheet plates which are opposite to each other, the midpoint of the connection of the two plates coincides with the center of the rotating shaft, and the rear rotating plate is placed along the vertical axis when the cage is locked.

Preferably, embedding grooves are provided at left and/or right inner walls of the window.

More preferably, the embedding groove is a quadrangular prismatic groove.

Preferably, the number of the windows is one, two or more.

Preferably, the windows are arranged in the vertical axis direction.

Preferably, the locking member is used for locking the screw.

More preferably, at least two screw fixing holes are disposed around the locking member in the same diameter, and a radius of the front rotating plate is larger than the distance from the rotating shaft to the screw fixing hole, and a number of notches corresponding to the screw fixing holes are provided. The number of notches on the front rotating plate is the same as the number of the screw fixing holes.

The radius of the front rotating plate refers to a distance from the center of the rotating shaft to the farthest outer edge of the front rotating plate.

The distance from the rotating shaft to the screw fixing hole refers to the distance from the center of the rotating shaft to the edge of the screw fixing hole.

More preferably, the locking members are respectively provided with a screw fixing hole at two sides thereof in a transverse axis direction, the locking member includes a rotating plate and a rotating shaft, two notches are symmetrically provided on the rotating plate, a diameter of the rotating plate is larger than a distance between two adjacent screw fixing holes in the transverse axis direction, and a distance between the two notches is smaller than or equal to the distance between two adjacent screw fixing holes in the transverse axis direction.

Preferably, the projection of the plate body in usage state on the coronal plane is rectangle, and a projection on the horizontal plane is an arc.

To achieve the second object, a technical solution applied by the present disclosure is as follows.

The anterior cervical fixation and fusion system maintaining natural height is provided, including the aforementioned fixing plate and a fusion cage;

Preferably, the locking member is used for locking the fusion cage.

More preferably, the front surface of the cage is pressed by the locking member during use.

Preferably, the locking member includes a front rotating plate, a rear rotating plate and a rotating shaft, the front rotating plate for locking the screw is at the front side of the plate body, the rear rotating plate is at the rear side of the plate body, and the rear rotating plate is locked on the front surface of the fusion cage in the use state.

More preferably, when the cage is locked, the length direction of the rear rotating plate coincides with the direction of the vertical axis.

Preferably, in the use state, the front surface of the fusion cage is flush with the front surface of the fixing plate, the locking member includes a rotating plate and a rotating shaft, and opening and closing of the window are performed by rotating the locking member to control a locking state of the fusion cage.

More preferably, three notches are symmetrically arranged on the front rotating plate, so that opening and closing of the window and two screw fixing holes are performed by rotating the locking member to control the locking state of the fusion cage and screws.

Preferably, embedding grooves are provided at left and/or right inner walls of the window of the fixing plate, the fusion cage is provided with embedding teeth matched with the embedding grooves, and in the use state, the embedding grooves and the embedding teeth are matched to fix the fusion cage on upper and/or lower vertebral bodies.

More preferably, each side of the locking member is provided with a screw fixing hole in the horizontal axis direction, the locking member includes a front rotating plate and a rotating shaft, two notches are symmetrically provided on the front rotating plate, the diameter of the front rotating plate is larger than a distance between two adjacent screw fixing holes in the transverse axis direction, and a distance between the two notches is smaller than or equal to the distance between two adjacent screw fixing holes in the transverse axis direction.

Preferably, the cervical vertebra anterior fixation and fusion system maintaining natural height also includes screws.

To achieve the third object, a technical solution applied by the present disclosure is as follows.

A method for anterior cervical discectomy and fusion (ACDF) includes the following steps: after removing the intervertebral disc, the vertebral body is fixed by using the fixing plate as any one of the above implementations, and then the fusion cage is implanted into the intervertebral disc position through the window.

Preferably, the method also includes any one of the following steps: cutting to form an incision; exposing front of a vertebral body and an intervertebral disc; positioning; opening the vertebral body and resetting; and suturing the incision.

Preferably, fixing with the fixing plate includes placing the plate body according to a physiological curvature of the cervical vertebra and fixing the plate body with a screw.

More preferably, fixing with the fixing plate further includes: rotating the locking member such that the rear surface of the rotating plate to press the front surface of the screw cap.

Preferably, implanting the fusion cage further includes: after implanting the fusion cage, the embedding teeth of the fusion cage are embedded in the embedding grooves of the fixing plate.

More preferably, implanting the fusion cage further includes: enabling the front surface of the fusion cage to be flush with the front surface of the fixing plate.

More preferably, implanting the fusion cage further includes: rotating the locking member to enable the rear surface of the rotating plate to press the front surface of the corresponding fusion cage and front surfaces of two screw caps.

Preferably, implanting the fusion cage further includes: after implanting the fusion cage, rotating the locking member such that a rear rotating plate presses the front surface of the corresponding fusion cage while the front rotating plate presses the front surfaces of corresponding two screw caps.

The inventor of the present application designs a new surgical method for the technical problem that the space of the cervical vertebrae is distracted too large due to the fusion cage and thus causes the cervical vertebra to lose its natural height during the cervical discectomy, thereby causing the postoperative pain. The inventor provides a new surgical method that after the disc is removed, the vertebral body is fixed and then the cage is implanted. The method overcomes the defect that the neck pain is caused by lost natural height because the vertebral body is distracted too much by the implanted fusion cage. Based on this, the fixing plate and the anterior cervical fixation and fusion system maintaining natural are designed. The instrument of the present disclosure has the advantages that:

1. The window of the fixing plate, is designed to be large enough, which breaks with convention and allows the fusion cage to pass through the window;

2. The locking member is provided with a rear rotating plate, wherein the rear surface of the rear rotating plate can just press the front surface of the fusion cage to fix the fusion cage so as to prevent the fusion cage from falling off or being displaced, and thus the stability of the system is improved;

3. The left and right surfaces of the fusion cage are respectively provided with embedding teeth which are matched with embedded grooves of the fixing plate, so that the fusion cage is firmly fixed at the intervertebral disc position, and the fusion cage can share stress to enable the reconstructed cervical vertebra system to be uniformly and stably stressed;

4. The front surface of the fusion cage is flush with the front surface of the fixing plate during use, and the stability of the system is further improved by the limit of the locking member.

The present disclosure is helpful to improve the surgical effect of the cervical disc resection.

Reference numbers and components referred to in the drawings are as follows: 100: fixing plate; 1: plate body; 2: window; 3: locking member; 31: rotating plate; 311: front rotating plate; 312: rear rotating plate; 3121: pressing plate; 32: rotating shaft; 33: notch; 4: screw fixing hole; 5: embedding groove; 200: fusion cage; 6: bone implanted hole; 7: locking tooth; 8: embedding tooth. Throughout the specification mention is made of the screws that one of skill in the art would know are designed to be accommodated in the screw fixing holes 4; however for clarity sake the screws are not shown in any of the figures despite their function and use in the fixing plate being described throughout the specification.

DETAILED DESCRIPTION

With consideration and summary in long-term clinical work, the inventor of the present application has realized that a fusion cage causes the interbody to be opened too much and thus causes the cervical vertebra to lose its natural height during the cervical discectomy, and then causes a pain in the postoperative neck. Thus, the inventor consequently designs a new surgical method, that is, fixing a vertebral body by a fixing plate in advance, and then placing a fusion cage for bone implanting, and also designs a new fixing plate and a fixation and fusion system. The following detailed description of the embodiments of the present disclosure is provided in conjunction with the accompanying drawings. The described embodiments are only some but not all embodiments of the present disclosure, and the technical features of the following embodiments may be arbitrarily combined.

Figure 12:
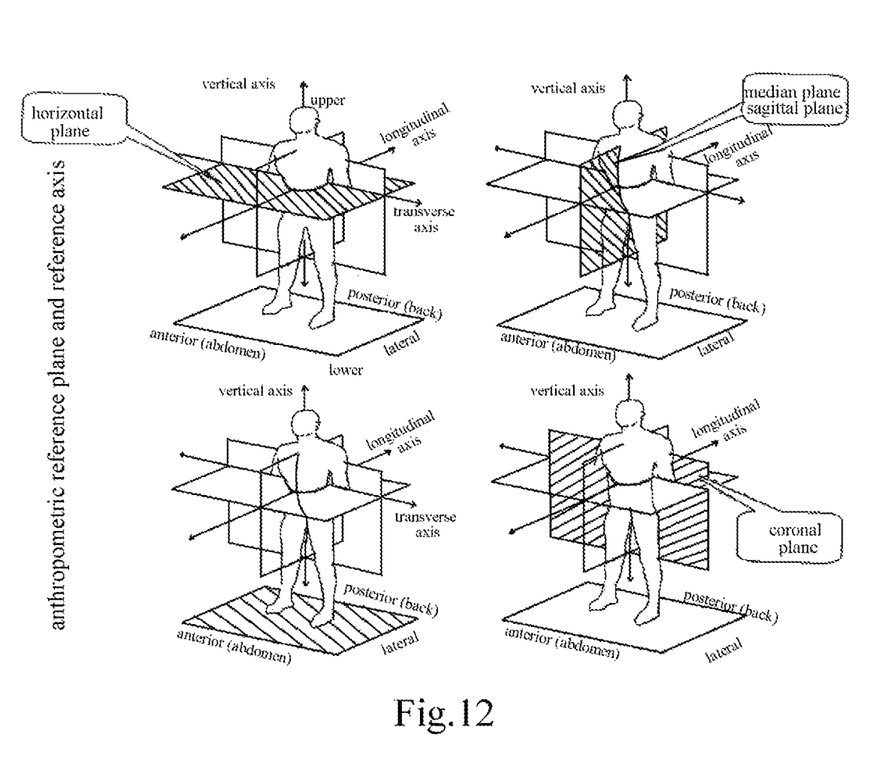
FIG. 12 is a schematic view of an anthropometric reference plane and a reference axis.

In the following description of the embodiments, the terms "vertical axis", "longitudinal axis", "transverse axis", "coronal plane", "horizontal plane", "sagittal plane", and the terms "anterior", "posterior", "upper" and "lower" are defined according to the anthropometric reference plane and a reference axis with particular reference to FIG. 12, in view of a usage state of the device of the present disclosure.

First Embodiment: Fixing Plate of the First Example

Figure 1:
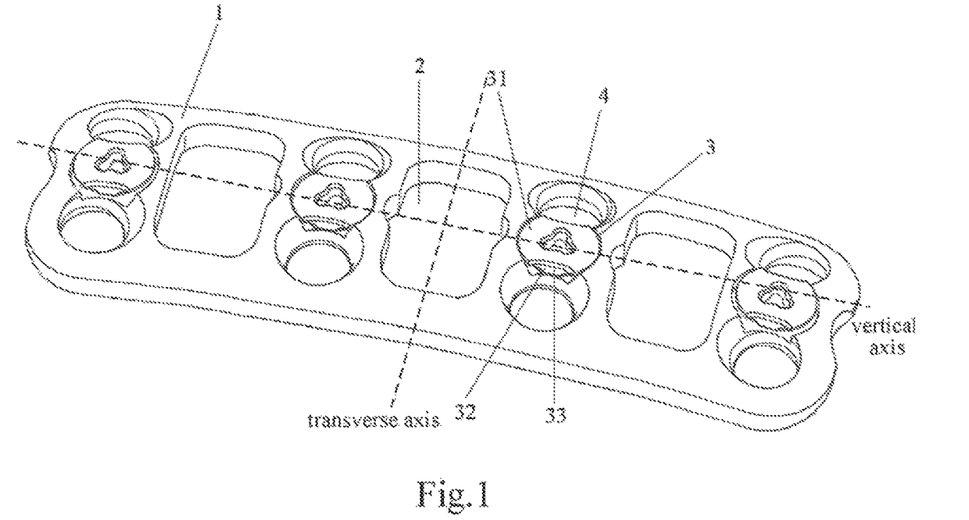
FIG. 1 is a schematic structural view of a fixing plate of a first embodiment.

FIG. 1 is a schematic structural view of a fixing plate of the first embodiment. The fixing plate is provided with a plate body 1, windows 2, locking members 3 and screw fixing holes 4. The projection of the plate body 1 in the state of use is rectangular on the coronal plane (the outline is substantially rectangular), and the projection on the horizontal plane is an arc. The plate body 1 is provided with three windows 2 arranged along the vertical axis direction. The projection of the window 2 on a coronal plane presents a rectangle (the outline of the window 2 is basically rectangular). The minimum distance between an upper side wall and a lower side wall of the window 2 in the vertical axis direction is 3-8 mm, and the minimum distance between a left side wall and a right side wall of the window 2 in a transverse axis direction is 12.1-18 mm. Locking members 3 are respectively provided at both ends of the plate body 1 and between two adjacent windows 2, and two sides of each locking member 3 in the transverse axis direction are respectively provided with a screw fixing hole 4 matched with a screw. The locking member 3 is riveted on the plate body 1 and includes a rotating plate 31 and a rotating shaft 32. Two notches 33 are symmetrically formed on the rotating plate 31. A diameter of the rotating plate 31 is larger than a distance between two adjacent screw fixing holes 4 in the transverse axis direction, and a distance between two notches 33 is smaller than or equal to the distance between two adjacent screw fixing holes 4 in the transverse axis direction.

It should be noted that the function of the conventional windows of the fixing plate includes: acting as a bone implanting window for filling a bone into the position of the intervertebral disc; allowing blood to overflow from the intervertebral disc; and acting as a viewing window for observing whether the fusion cage and the fixing plate are correctly placed. The size of the conventional window of the fixing plate is as follows: the minimum distance between the upper side wall and the lower side wall in the vertical axis direction is 4-6 mm, and the minimum distance between the left side wall and the right side wall in the transverse axis direction is 10-12 mm. Thus, the size is relatively small without allowing the fusion cage to pass through, as a result of comprehensively considering the above purposes and ensuring that the fixing plate can provide a large and uniform stress to the vertebral body. Based on this new surgical method, the present disclosure needs to insert the fusion cage through the window 2 after the fixing plate is fixed, so the window 2 of the fixing plate of the present disclosure is designed to be larger and different from the conventional specification. Preferably, the minimum distance between the upper side wall and the lower side wall in the vertical axis direction is 3-8 mm, and the minimum distance between the left side wall and the right side wall of the window in the transverse axis direction is 12.1-18 mm, and more preferably, the minimum distance between the upper side wall and the lower side wall in the vertical axis direction is 4-8 mm, and the minimum distance between the left side wall and the right side wall of the window in the transverse axis direction is 14-18 mm. By this method, a height of the vertebral body is limited by using a fixing plate, and then a fusion cage is implanted, so that the height of the vertebral body cannot be increased under the limit of the fixing plate, and the natural height is maintained, and further avoiding the complication such as pain of postoperative neck; and in addition, the fusion cage, the upper vertebral body and the lower vertebral body are firmly extruded to facilitate the osteogenesis.

A shape of the plate body 1 is not limited by this embodiment, and may be in other shapes, wherein the plate body 1 is designed to have an arc-shaped projection on a horizontal plane in a use state, so as to better fit the cervical vertebra. The plate body 1 may be made of any material applied for clinically, such as stainless steel, titanium alloy, high molecular polymer material, etc.

The screw fixing holes 4 are used to be matched with screws to fix the fixing plate on the vertebral body. The locking member 3 is used for locking at a front surface of a screw cap of the screw to prevent the screw from shifting in the using process, and maintain the stability of the whole system. The position, number, shape and configuration of the screw fixing hole 4, and the position, number, shape and configuration of the locking member 3 are not limited to the embodiment.

Second Embodiment: Fixing Plate of Second Example

Figure 2:
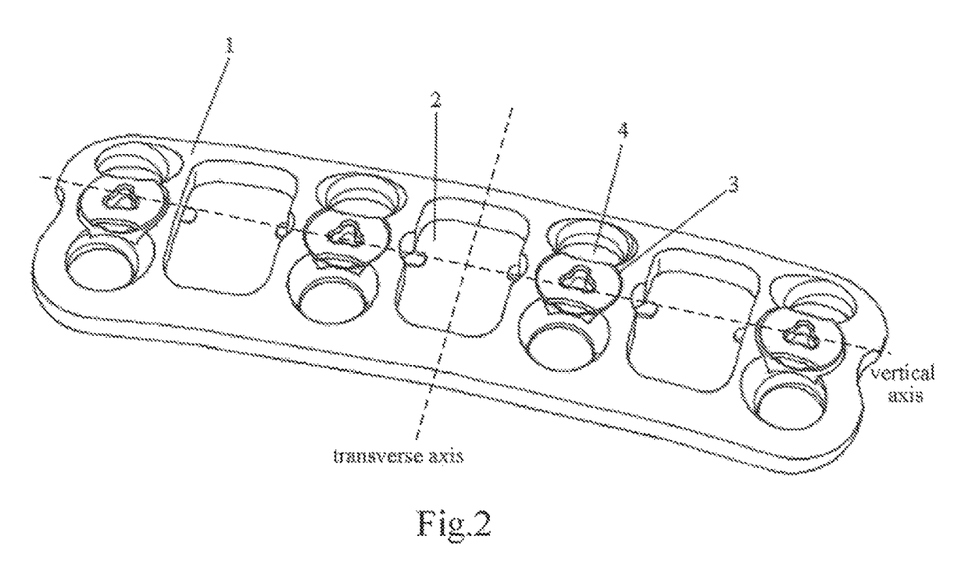
FIG. 2 is a schematic structural view of a fixing plate of a second embodiment.

FIG. 2 is a schematic structural view of a fixing plate of a second embodiment. The fixing plate is provided with a plate body 1, windows 2, locking members 3 and screw fixing holes 4. The projection of the plate body 1 in the state of use is rectangular on the coronal plane (the outline is substantially rectangular), and the projection on the horizontal plane is an arc. The plate body 1 is provided with three windows 2 arranged along the vertical axis direction. The projection of the window 2 on a coronal plane presents a rectangle (the outline of the window 2 is basically rectangular). The minimum distance between an upper side wall and a lower side wall of the window 2 in the vertical axis direction is 3-8 mm, and the minimum distance between a left side wall and a right side wall of the window 2 in the transverse axis direction is 12.1-18 mm. Locking members 3 are respectively provided at both ends of the plate body 1 and between two adjacent windows 2, and two sides of each locking member 3 in the transverse axis direction are respectively provided with a screw fixing hole 4 matched with a screw.

Figure 3A:
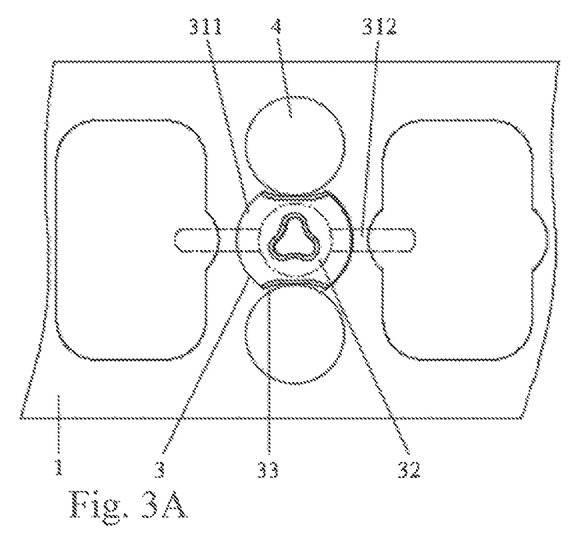
FIGS. 3A and 3B are schematic structural views of a locking member of the second embodiment, wherein the FIG. 3A shows that screw fixing holes are open; and the FIG. 3B shows that screw fixing holes are all closed, and a window is open.
Figure 3B:
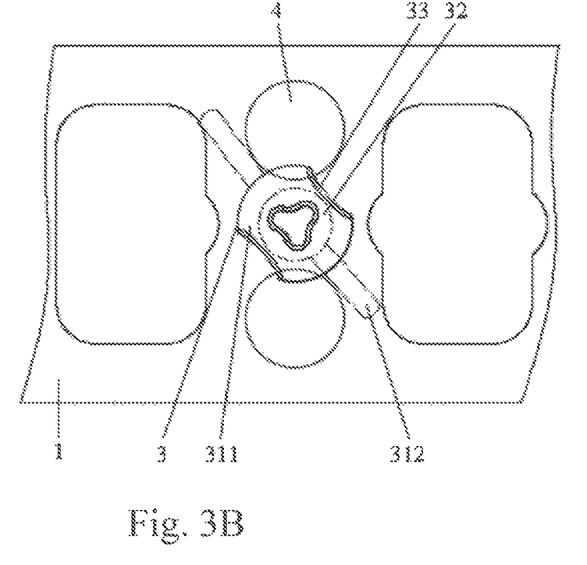

FIGS. 3A and 3B are schematic structural views of a locking member of the second embodiment. The locking member 3 is riveted on the plate body 1 and includes a front rotating plate 311, a rear rotating plate 312 and a rotating shaft 32, wherein the front rotating plate 311 is at a front side of the plate body 1, and the rear rotating plate 312 is at a rear side of the plate body 1. Two notches 33 are symmetrically formed on the front rotating plate 311. A diameter of the front rotating plate 311 is larger than a distance between two adjacent screw fixing holes 4 in the transverse axis direction, and a distance between two notches 33 is smaller than or equal to the distance between two adjacent screw fixing holes 4 in the transverse axis direction. The rear rotating plate 312 is a rounded rectangle, and a length direction of the rear rotating plate is the same as the vertical axis direction when the fusion cage is locked.

The front surface of the fusion cage does not extend beyond the surface of the vertebral body after implanting of the conventional fusion cage into the position of intervertebral disc. In this embodiment, a rear side of the locking member 3 is further provided with a rear rotating plate 312. By rotating the locking member 3, a rear surface of the rear rotating plate 312 may just press the front surface of the fusion cage to fix the fusion cage, so as to prevent the escape or displacement of fusion cage, which helps to improve the stability of the system.

Third Embodiment: Fixing Plate of Third Example

Figure 4:
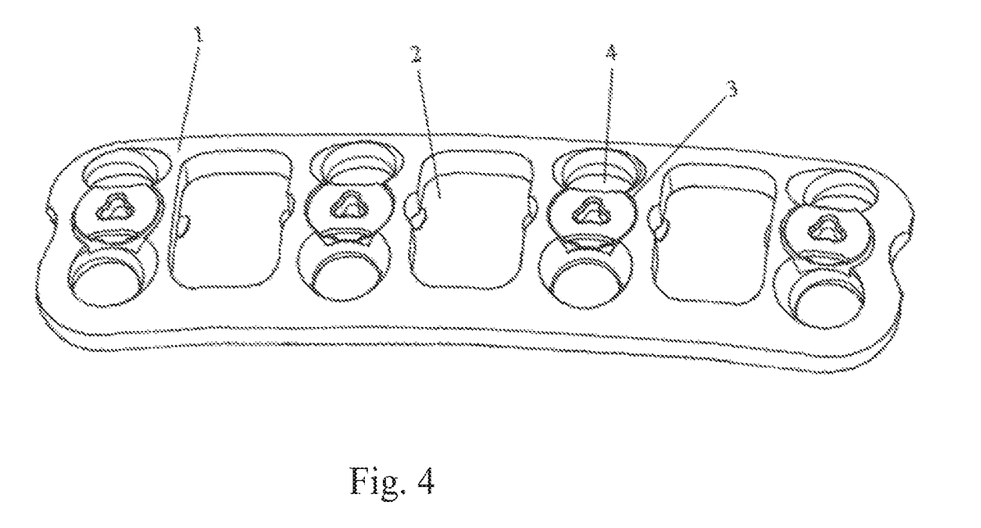
FIG. 4 is a schematic structural view of a fixing plate of a third embodiment.

FIG. 4 is a schematic structural view of a fixing plate of the third embodiment. The fixing plate is provided with a plate body 1, windows 2, locking members 3 and screw fixing holes 4. The projection of the plate body 1 in the state of use is rectangular on the coronal plane (the outline is substantially rectangular)-, and the projection of the plate body 1 on a horizontal plane presents an arc. The plate body 1 is provided with three windows 2 arranged in the vertical axis direction. A projection of the window 2 on a coronal plane presents a rectangle (the outline of the window 2 is basically rectangular). The minimum distance between an upper side wall and a lower side wall of the window 2 in the vertical axis direction is 3-8 mm, and the minimum distance between the left side wall and the right side wall of the window 2 in the transverse axis direction is 12.1-18 mm. Locking members 3 are respectively provided at two ends of the plate body 1 and between two adjacent windows 2, the two sides of each locking member 3 in the transverse axis direction are respectively provided with a screw fixing hole 4 matched with a screw.

Figure 5A:
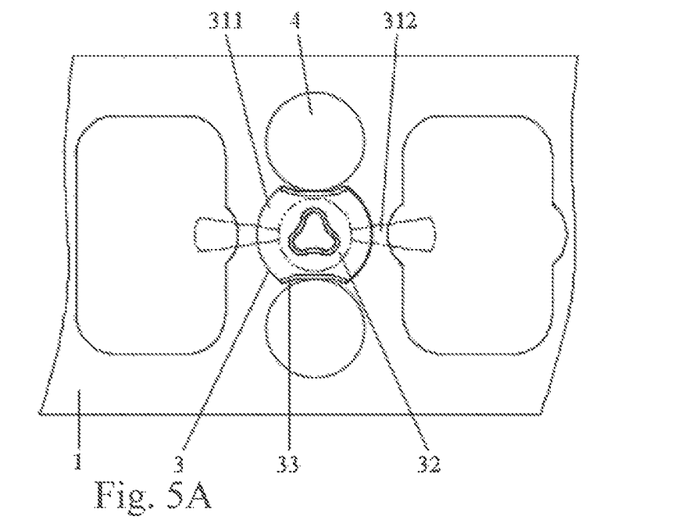
FIGS. 5A and 5B are schematic structural views of a locking member of the third embodiment, wherein the FIG. 5A shows that screw fixing holes are open; and the FIG. 5B shows that screw fixing holes are all closed, and a window is open.
Figure 5B:
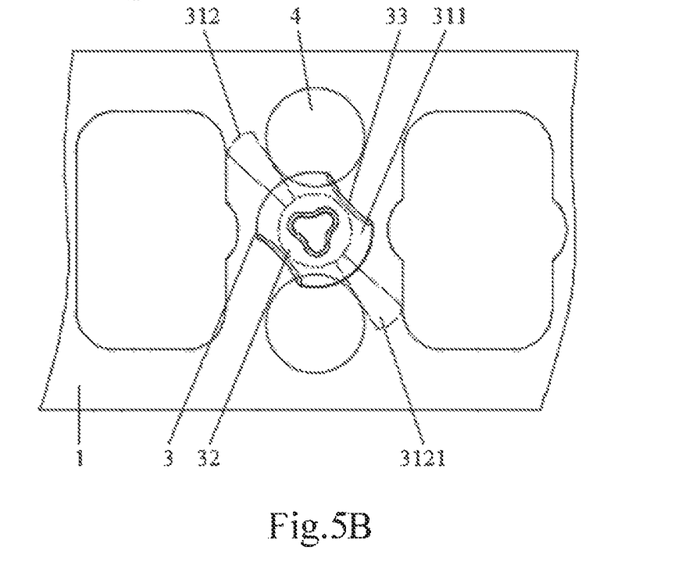

FIGS. 5A and 5B are schematic structural views of a locking member of the third embodiment. The locking member 3 includes a front rotating plate 311, a rear rotating plate 312 and a rotating shaft 32, wherein the locking member 3 is riveted on the plate body 1, the front rotating plate 311 is at a front side of the plate body 1, and the rear rotating plate 312 is at a rear side of the plate body 1. Two notches 33 are symmetrically formed on the front rotating plate 311. A diameter of the front rotating plate 311 is larger than a distance between two adjacent screw fixing holes 4 in the transverse axis direction, and a distance between two notches 33 is smaller than or equal to the distance between two adjacent screw fixing holes 4 in the transverse axis direction. The rear rotating plate 312 is composed of two fan-shaped sheet pressing plates 3121 which are opposite to each other. The midpoint of a connecting position of two pressing plates 3121 coincides with the axis of the rotating shaft 32, and a direction of a bisector (horizontal direction) of two pressing plates 3121 is consistent with the vertical axis direction when the fusion cage is locked.

In this embodiment, a contact area of the rear rotating plate 312 and the fusion cage is larger, so that the effect of limiting the displacement of the fusion cage is more prominent.

Fourth Embodiment: Cervical Vertebra Anterior Fixation and Fusion System Maintaining Natural Height of First Example The cervical vertebra anterior fixation and fusion system maintaining natural height of the embodiment includes a fixing plate 100 and a fusion cage 200.

Figure 6:
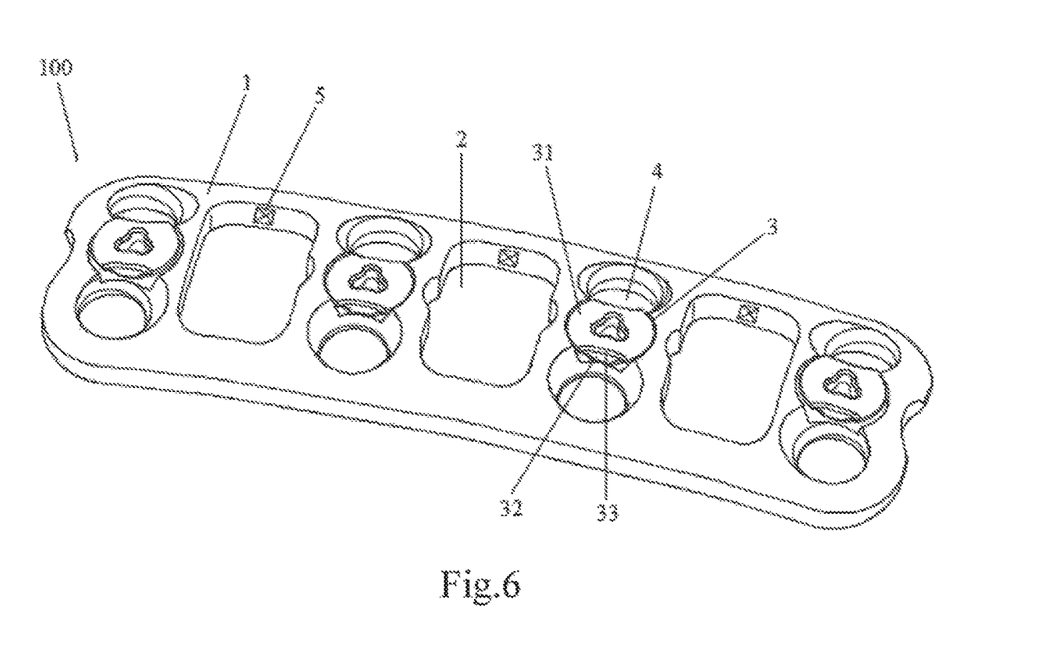
FIG. 6 is a schematic structural view of a fixing plate of the fourth embodiment.

FIG. 6 is a schematic structural view of a fixing plate of a fourth embodiment. The fixing plate 100 is provided with a plate body 1, windows 2, locking members 3 and screw fixing holes 4. The projection of the plate body 1 in the state of use is rectangular on the coronal plane (the outline is substantially rectangular), and the projection of the plate body 1 on a horizontal plane presents an arc. The plate body 1 is provided with three windows 2 arranged in the vertical axis direction, and a projection of the window 2 on a coronal plane presents a rectangle (The outline of the windows 2 is basically rectangular). The minimum distance between an upper side wall and a lower side wall of the window 2 in the vertical axis direction is 3-8 mm, and the minimum distance between a left side wall and a right side wall of the window 2 in the transverse axis direction is 12.1-18 mm. The left side wall and the right side wall of the window 2 are respectively provided with an embedding groove 5 which is a quadrangular prismatic groove. Locking members 3 are respectively provided at two ends of the plate body 1 and at positions between two adjacent windows 2, and two sides of each locking member 3 in the transverse axis direction are respectively provided with a screw fixing hole 4 matched with a screw. The locking member 3 includes a rotating plate 31 and a rotating shaft 32, and is riveted on the plate body 1. Two notches 33 are symmetrically formed on the rotating plate 31. A diameter of the rotating plate 31 is larger than a distance between two adjacent screw fixing holes 4 in the transverse axis direction, and a distance between two notches 33 is smaller than or equal to the distance between two adjacent screw fixing holes 4 in the transverse axis direction.

Figure 7:
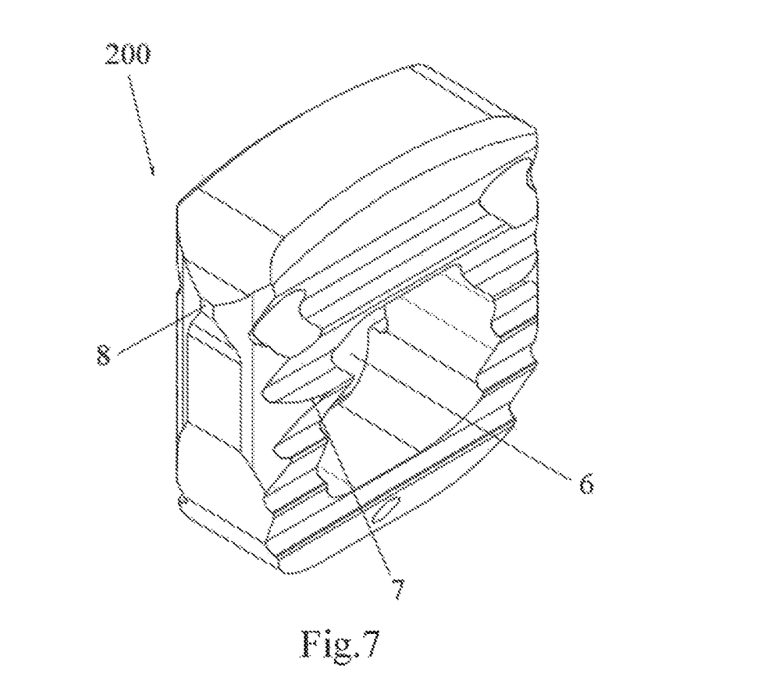
FIG. 7 is a schematic structural view of a fusion cage of the fourth embodiment.

FIG. 7 is a schematic structural view of a fusion cage of the fourth embodiment. The fusion cage 200 is provided with a bone implanted hole 6, the surface of the cage 200 that is in contact with the upper and lower vertebral bodies is provided with a locking tooth 7, and embedding teeth 8 are respectively provided at left and right surfaces of the fusion cage 200. The embedding tooth 8 is a quadrangular prismatic protrusion, and embedding teeth 8 are matched with embedding grooves 5 of the fixing plate 100 (see FIG. 8).

Figure 8:
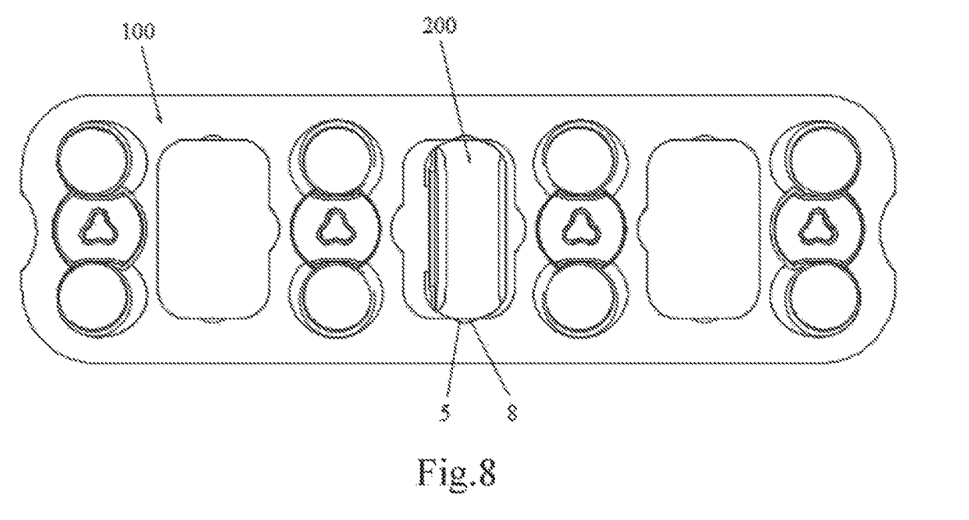
FIG. 8 is a schematic assembly view of the fixing plate and the fusion cage of the fourth embodiment.

A method for performing anterior cervical discectomy and fusion (ACDF) by applying the fixation and fusion system includes the following steps:

Step 1: cutting to form an incision;

Step 2: exposing front of a vertebral body and an intervertebral disc;

Step 3: positioning;

Step 4: distracting the vertebral body and resetting;

Step 5: removing the intervertebral disc;

Step 6: fixing with a fixing plate, wherein the plate body 1 is placed according to a physiological curvature of the cervical vertebra and fixed by a screw, and then a locking member 3 is rotated to enable a rear surface of the rotating plate 31 to press a front surface of a screw cap;

Step 7: implanting a fusion cage, inserting a bone block in the bone implanted hole 6 of the fusion cage 200, then the fusion cage 200 is implanted into an intervertebral disc position, and after the implanting, the embedding teeth 8 of the fusion cage 200 are embedded into embedding grooves 5 of the fixing plate 100; and Step 8: suturing the incision.

In this embodiment, on one hand, based on the new surgical method as mentioned above, a height of a vertebral body is limited by using a fixing plate 100, and then a fusion cage 200 is implanted, so that the height of the vertebral body cannot be increased under the limit of the fixing plate 100, and the natural height is maintained, avoiding the complication such as pain of postoperative neck, and firmly extruding the fusion cage, the upper vertebral body and the lower vertebral body to facilitate osteogenesis; on the other hand, the length of the fusion cage 200 in the longitudinal direction is relatively large, and the fusion cage 200 is firmly fixed at the intervertebral disc position by matching engaging teeth 8 on the left and right sidewalls with engaging grooves 5 of the fixing plate 100, so that the fusion cage 200 may share the stress on the vertebral body from the fixing plate 100.

The fusion cage 200 may be in any shape, such as rectangular or shuttle-shaped.

Fifth Embodiment: Cervical Vertebra Anterior Fixation and Fusion System Maintaining Natural Height of Second Example The cervical vertebra anterior fixation and fusion system maintaining natural height of this embodiment includes a fixing plate 100, a fusion cage 200 and screws.

Figure 9:
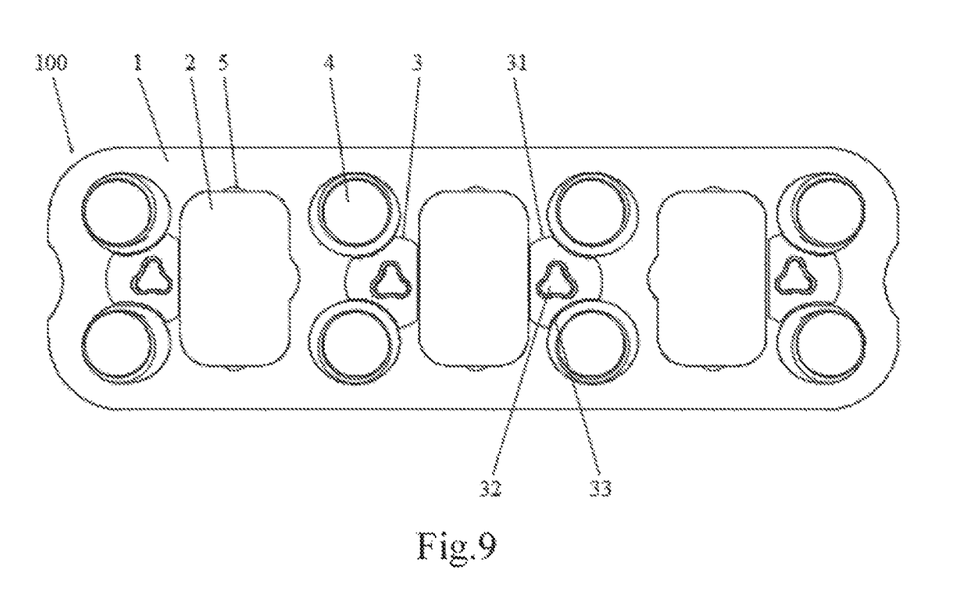
FIG. 9 is a schematic structural view of a fixing plate of a fifth embodiment.

FIG. 9 is a schematic structural view of a fixing plate of the fifth embodiment. The fixing plate 100 is provided with a plate body 1, windows 2, locking members 3 and screw fixing holes 4. The projection of the plate body 1 in the state of use is rectangular on the coronal plane (the outline is substantially rectangular), and the projection on the horizontal plane presents an arc. The plate body 1 is provided with three windows 2 arranged in the vertical axis direction, and the projection of the window 2 on the coronal plane presents a rectangle (the outline of the windows 2 is basically rectangular). The minimum distance between an upper side wall and a lower side wall of the window 2 in the vertical axis direction is 3-8 mm, and the minimum distance between a left side wall and a right side wall of the window 2 in the transverse axis direction is 12.1-18 mm. The left side wall and the right side wall of the window 2 are respectively provided with an embedding groove 5 which is a quadrangular prismatic groove. Locking members 3 are respectively provided at two ends of the plate body 1 and at positions between two adjacent windows 2, two sides of each locking member 3 in the transverse axis direction are respectively provided with a screw fixing hole 4 matched with a screw. The locking member 3 is at a central position of the connecting region of the window 2 and two screw fixing holes 4. The locking member 3 is riveted on the plate body 1 and includes a rotating plate 31 and a rotating shaft 32, and three notches 33 are symmetrically formed on the rotating plate 31, so that the window 2 and the two screw fixing holes 4 can be opened and closed by rotating the locking member 3.

Figure 10:
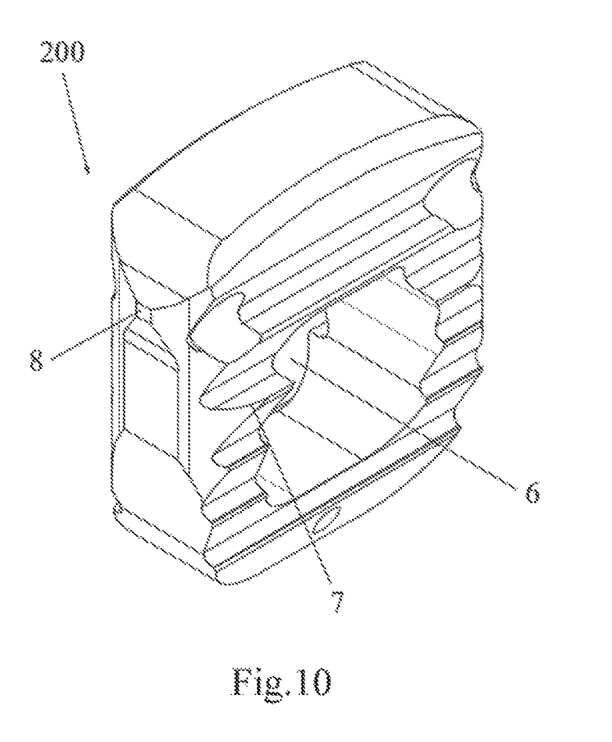
FIG. 10 is a schematic structural view of a fusion cage of the fifth embodiment.

FIG. 10 is a schematic structural view of the fusion cage of the fifth embodiment. The fusion cage 200 is provided with the bone implanted hole 6, the surface of the cage 200 that is in contact with the upper and lower vertebral bodies is provided with a locking tooth 7, and embedding teeth 8 are respectively provided at left and right surfaces of the fusion cage 200. The embedding tooth 8 is a quadrangular prismatic protrusion, and embedding teeth 8 are matched with embedding grooves 5 of the fixing plate 100.

A method for performing anterior cervical discectomy and fusion (ACDF) by applying the fixation and fusion system includes the following steps:
  Step 1: cutting to form an incision;
  Step 2: exposing front of the vertebral body and the intervertebral disc;
  Step 3: positioning;
  Step 4: distracting the vertebral body and resetting;
  Step 5: removing the intervertebral disc;
  Step 6: fixing with a fixing plate, wherein the plate body 1 is placed according to the physiological curvature of the cervical vertebra and fixed by a screw;
  Step 7: implanting a fusion cage, inserting a bone block in the bone implanted hole 6 of the fusion cage 200, then the fusion cage 200 is implanted into the intervertebral disc position, the embedding teeth 8 of the fusion cage 200 are embedded into embedding grooves 5 of the fixing plate 100 after the implanting, and simultaneously, the front surface of the fusion cage 200 is flush with the front surface of the fixing plate 100, and then the locking member 3 is rotated to enable the rear surface of the rotating plate 31 to press the front surface of the corresponding fusion cage 200 and the front surfaces of two screw caps; and
  Step 8: suturing the incision.

In this embodiment, the front surface of the fusion cage 200 in a use state is designed to be flush with the front surface of the fixing plate 100, and thus the locking member 3 is further limited, thereby further improves the stability of the system. In this embodiment, the stress provided for the fusion cage 200 by the fixing plate 100 is also dispersed by the vertebral body, and the force of whole reconstructed cervical vertebra system is uniform and so it is stably.

Sixth Embodiment: Cervical Vertebra Anterior Fixation and Fusion System Maintaining Natural Height of Third Example The cervical vertebra anterior fixation and fusion system maintaining natural height of this embodiment includes a fixing plate 100, a fusion cage 200 and screws.

The fixing plate 100 is as described in the third embodiment.

Figure 11:
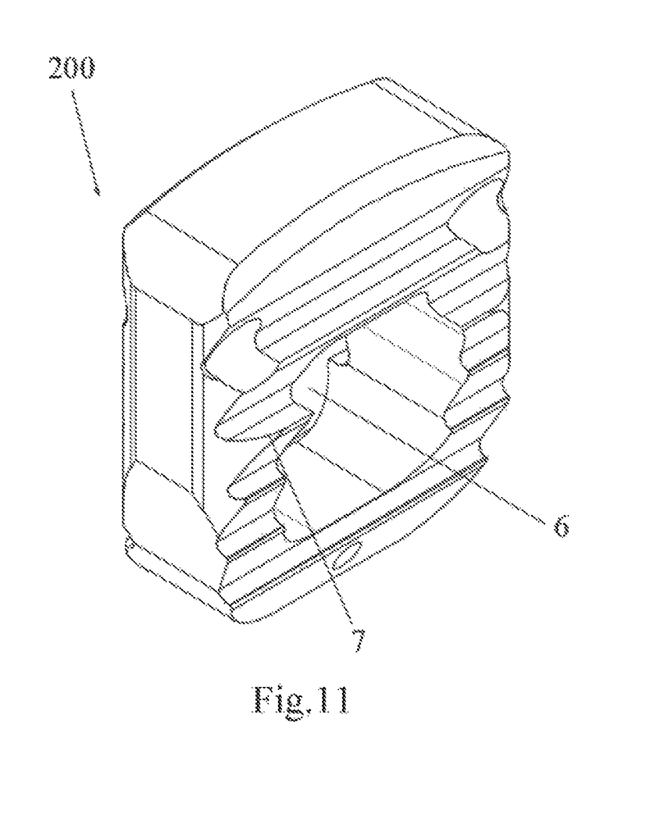
FIG. 11 is a schematic structural view of a fusion cage of a sixth embodiment.

FIG. 11 is a schematic structural view of a fusion cage of the sixth embodiment. The fusion cage 200 is provided with a bone implanted hole 6, the surface of the cage 200 that is in contact with the upper and lower vertebral bodies is provided with a locking tooth 7.

A method for performing ACDF by applying the fixation and fusion system includes the following steps:
  Step 1: cutting to form an incision;
  Step 2: exposing front of a vertebral body and an intervertebral disc;
  Step 3: positioning;
  Step 4: distracting the vertebral body and resetting;
  Step 5: removing the intervertebral disc;
  Step 6: fixing with a fixing plate, wherein the plate body 1 is placed according to a physiological curvature of the cervical vertebra and fixed by a screw;
  Step 7: implanting a fusion cage, inserting a bone block in the bone implanted hole 6 of the fusion cage 200, then the fusion cage 200 is implanted into an intervertebral disc position, and after the implanting, the locking member 3 is rotated such that a rear rotating plate 312 presses the front surface of the corresponding fusion cage 200 while the front rotating plate 311 presses front surfaces of corresponding two screw caps; and
  Step 8: suturing the incision.

In this embodiment, the front surface of the fusion cage 200 is pressed by the rear rotating plate 312, so that the fusion cage is prevented from being displaced, and the stability of the system is improved.

The above description refers to only some preferred embodiments of the present disclosure, and it should be noted that several modifications and additions may be made by those skilled in the art without departing from the method of the present disclosure, and these modifications and additions should be considered as being within the protection scope of the present disclosure.

What is claimed is:

1. A cervical vertebra fixation and fusion system comprising: a plate body which is provided with a plurality of windows, a plurality of locking members each associated with at least one of a plurality of screw fixing holes, each screw fixing hole adapted to receive a screw; and wherein each of said windows is sized to allow a cervical implant to pass at least partially through said window,
  wherein said cervical implant is a fusion cage that is adapted to be locked in place by at least one of said locking members;
  a front surface of said fusion cage is pressed by at least one of said locking members when in use.

2. The cervical vertebra fixation and fusion system according to claim 1, wherein each of said locking members comprises a front rotating plate and a rotating shaft, and wherein said front rotating plate is disposed on a front side of said plate body.

3. The cervical vertebra fixation and fusion system according to claim 2, wherein each of said locking members also comprises a rear rotating plate disposed on a rear side of said plate body and rotates around said rotating shaft, and wherein said rear rotating plate is locked on the front surface of the fusion cage when in use.

4. The cervical vertebra fixation and fusion system according to claim 3, wherein said rear rotating plate is composed of two parts which are opposite to each other.

5. The cervical vertebra fixation and fusion system according to claim 3, wherein said rear rotating plate is one of a chamfered rectangular sheet or a pair of fan-shaped sheet pressing plates.

6. The cervical vertebra fixation and fusion system according to claim 3, wherein one of said plurality of screw fixing holes are disposed on each side of each of said locking members along a horizontal axis direction, and Wherein at least two notches are provided on said front rotating plate of said locking member, a diameter of said front rotating plate being larger than a distance between two adjacent screw fixing holes in a transverse axis direction, and wherein a distance between said two notches is smaller than or equal to said distance between two adjacent screw fixing holes in said transverse axis direction.

7. The cerebral vertebra fixation and fusion system according to claim 1, wherein embedding grooves are provided at left and/or right inner walls of each of said plurality of windows.

8. The cerebral vertebra fixation and fusion system according to claim 7, wherein each of said embedding grooves is a quadrangular prismatic groove.

9. The cerebral vertebra fixation and fusion system according to claim 7, wherein said fusion cage is provided with embedding teeth that can engage with said embedding grooves, and wherein in use said embedding grooves and said embedding teeth are matched to secure said fusion cage on upper and/or lower vertebral bodies.

10. The cerebral vertebra fixation and fusion system according to claim 1, wherein a number of said plurality of windows is two.

11. The cervical vertebra fixation and fusion system according to claim 1, wherein a minimum distance between an upper side wall and a lower side wall of each of said windows in a vertical axis direction is from 3 to 8 mm; and a minimum distance between a left side wall and a right side wall of each of said windows in a transverse axis direction is from 12.1 to 18 mm.

* * * * *